(12) United States Patent
Sakamaki

(10) Patent No.: US 12,240,929 B2
(45) Date of Patent: Mar. 4, 2025

(54) PHOTOCURABLE COMPOSITION, DENTURE BASE, AND PLATE DENTURE

(71) Applicant: MITSUI CHEMICALS, INC., Tokyo (JP)

(72) Inventor: Toshikazu Sakamaki, Tokyo (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 18/316,322

(22) Filed: May 12, 2023

(65) Prior Publication Data

US 2023/0303746 A1  Sep. 28, 2023

Related U.S. Application Data

(63) Continuation of application No. 16/498,448, filed as application No. PCT/JP2018/013491 on Mar. 29, 2018, now Pat. No. 11,780,947.

(30) Foreign Application Priority Data

Mar. 29, 2017  (JP) ................. 2017-066065

(51) Int. Cl.
| | |
|---|---|
| C08F 222/10 | (2006.01) |
| A61C 13/087 | (2006.01) |
| A61K 6/887 | (2020.01) |
| C08F 2/48 | (2006.01) |
| C08F 20/30 | (2006.01) |
| C08F 220/18 | (2006.01) |

(52) U.S. Cl.
CPC ...... *C08F 222/1025* (2020.02); *A61C 13/087* (2013.01); *A61K 6/887* (2020.01); *C08F 2/48* (2013.01); *C08F 20/30* (2013.01); *C08F 222/1063* (2020.02); *C08F 220/1807* (2020.02)

(58) Field of Classification Search
CPC ....... A61C 13/087; A61K 6/887; A61L 27/16; C08F 2/48; C08F 20/30; C08F 220/1807; C08F 222/1025; C08F 222/1065; C08F 222/1063; C08F 220/1087; C08F 88/1063; C08F 220/301
See application file for complete search history.

(56) References Cited

U.S. PATENT DOCUMENTS

| | | | |
|---|---|---|---|
| 4,983,644 A | 1/1991 | Mukai et al. | |
| 5,008,300 A | 4/1991 | Makino et al. | |
| 5,182,332 A | 1/1993 | Yamamoto et al. | |
| 5,573,889 A | 11/1996 | Hofmann et al. | |
| 6,783,809 B2 | 8/2004 | Steinmann et al. | |
| 9,387,056 B2* | 7/2016 | Wachter | A61C 5/77 |
| 10,562,995 B2* | 2/2020 | Sakamaki | A61C 13/0013 |
| 10,639,887 B2* | 5/2020 | Sakai | B65H 20/02 |
| 2002/0127345 A1 | 9/2002 | Rheinberger et al. | |
| 2004/0131849 A1 | 7/2004 | Wires | |
| 2016/0332367 A1* | 11/2016 | Sun | B29C 64/40 |
| 2018/0014919 A1 | 1/2018 | Gomi et al. | |
| 2021/0038353 A1 | 2/2021 | Sakamaki | |

FOREIGN PATENT DOCUMENTS

| | | |
|---|---|---|
| EP | 3360907 A1 | 8/2018 |
| JP | H02004891 A | 1/1990 |
| JP | H02083307 A | 3/1990 |
| JP | H03063205 A | 3/1991 |
| JP | H06078937 A | 3/1994 |
| JP | 2002302523 A | 10/2002 |
| JP | 4160311 B2 | 10/2008 |
| WO | 2016125758 A1 | 8/2016 |
| WO | WO-2017061446 A1 * | 4/2017 ......... A61C 13/0013 |

OTHER PUBLICATIONS

Extended European Search Report issued on Oct. 1, 2020, by the European Patent Office in corresponding European Patent Application No. 18777868.3. (8 pages).

International Search Report (PCT/ISA/210) with an English translation, and Written Opinion (PCT/ISA/237) mailed on May 15, 2018, by the Japan Patent Office as the International Searching Authority for International Application No. PCT/JP2018/013491. (16 pages).

* cited by examiner

*Primary Examiner* — Sanza L. McClendon
(74) *Attorney, Agent, or Firm* — BUCHANAN INGERSOLL & ROONEY PC

(57) ABSTRACT

The present invention provides a photocurable composition for use in stereolithography, the photocurable composition including: a (meth)acrylic monomer (X) that is at least one selected from the group consisting of di(meth)acrylic monomers containing, within one molecule, two aromatic rings and two (meth)acryloyloxy groups, and that has a weight average molecular weight of from 400 to 580; a (meth) acrylic monomer (D) that is at least one selected from the group consisting of (meth)acrylic monomers containing, within one molecule, at least one aromatic ring and one (meth)acryloyloxy group, and that has a weight average molecular weight of from 140 to 350; and a photopolymerization initiator.

16 Claims, No Drawings

PHOTOCURABLE COMPOSITION, DENTURE BASE, AND PLATE DENTURE

CROSS-REFERENCE TO RELATED APPLICATIONS

This application is a continuation of U.S. patent application Ser. No. 16/498,448, filed on Sep. 27, 2019, which in turn is a U.S. national stage application of PCT/JP2018/013491, filed on Mar. 29, 2018, which claims priority to Japanese Patent Application No. 2017-066065, filed on Mar. 29, 2017, the entire contents of all of which are hereby incorporated by reference.

TECHNICAL FIELD

The present invention relates to a photocurable composition, a denture base, and a plate denture.

BACKGROUND ART

Conventionally, a denture base made of resin (referred to as "resin base") has been produced by a method in which a plaster mold adapted to an intraoral shape of a patient is first produced by a dental method, and then a curable resin is poured into the plaster mold, followed by curing the curable resin.

In recent years, a method has been proposed in which the intraoral shape of a patient is measured by a three-dimensional measurement and a denture base is produced based on the measured result, instead of the above described method utilizing a plaster mold, so as to reduce the number of hospital visits of patients and to allow for an efficient production of a denture base (see, for example, Japanese Patent Application Laid-Open (JP-A) No. H06-78937). Further, a method has also been proposed in which a dental prosthesis is produced using a three-dimensional printer (namely, a 3D printer) (see, for example, Japanese Patent (JP-B) No. 4160311).

SUMMARY OF INVENTION

Technical Problem

One example of the method of producing a stereolithographed product, preferably, a dental prosthesis, a medical device for intraoral use, or a tooth and jaw model (hereinafter, collectively referred to as "dental prosthesis or the like") using a 3D printer is a method referred to as "stereolithography", in which a photocurable composition is shaped in the form of a dental prosthesis or the like, and the resulting shaped product is then subjected to photocuring, to produce the dental prosthesis or the like.

In a case in which a stereolithographed product, preferably, a dental prosthesis or the like (a denture base, in particular) is produced by stereolithography, an excellent flexural strength (bending strength) and flexural modulus are required for the photocurable composition after being subjected to photocuring, in view of practical use. Further, in this case, an excellent fracture toughness may sometimes be required for the photocurable composition after being subjected to photocuring.

In other words, an object of one embodiment of the invention is to provide a photocurable composition which is used in stereolithography, and which has an excellent flexural strength and flexural modulus as well as an excellent fracture toughness after being subjected to photocuring.

Another object of one embodiment of the invention is to provide: a denture base which is a cured product of the above described photocurable composition and which has an excellent flexural strength and flexural modulus as well as an excellent fracture toughness; and a plate denture including the denture base.

Solution to Problem

The present inventors have found out, as a result of intensive studies, that a photocurable composition which contains a combination of specific monomer species and in which a specific functional group value (a) is within a specific range has an excellent flexural strength and flexural modulus as well as an excellent fracture toughness after being subjected to photocuring, and that the photocurable composition is particularly suitable for the production by stereolithography of a dental prosthesis or the like (in other words, a dental prosthesis, a medical device for intraoral use, or a tooth and jaw model), thereby completing the present invention.

In other words, specific means for solving the above described problems are as follows.

<1> A photocurable composition for use in stereolithography, the photocurable composition including:
a (meth)acrylic monomer (X) that is at least one selected from di(meth)acrylic monomers containing, within one molecule, two aromatic rings and two (meth)acryloyloxy groups, and that has a weight average molecular weight of from 400 to 580;
a (meth)acrylic monomer (D) that is at least one selected from (meth)acrylic monomers containing, within one molecule, at least one aromatic ring and one (meth)acryloyloxy group, and that has a weight average molecular weight of from 140 to 350; and
a photopolymerization initiator.

<2> The photocurable composition according to <1>, wherein at least one di(meth)acrylic monomer configuring the (meth)acrylic monomer (X) contains an ether bond within one molecule.

<4> The photocurable composition according to <1> or <2>, wherein the at least one di(meth)acrylic monomer configuring the (meth)acrylic monomer (X) contains from one to four ether bonds within one molecule.

The photocurable composition according to any one of <1> to <3>, wherein the at least one di(meth)acrylic monomer configuring the (meth)acrylic monomer (X) is a compound represented by the following Formula (x-1):

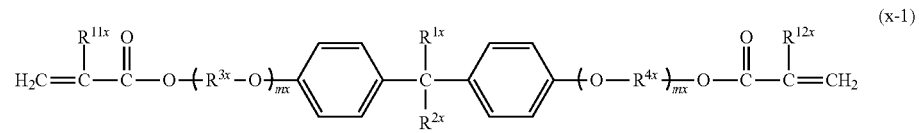

[wherein, in Formula (x-1), each of $R^{1x}$, $R^{2x}$, $R^{11x}$, and $R^{12x}$ independently represents a hydrogen atom or a methyl group; each of $R^{3x}$ and $R^{4x}$ independently represents a linear or branched alkylene group having from 2 to 4 carbon atoms; and each of mx and nx independently represents a number from 0 to 4, wherein mx and nx satisfy the relationship: $1 \le (mx+nx) \le 4$].

<5> The photocurable composition according to any one of <1> to <4>, wherein the at least one di(meth)acrylic monomer configuring the acrylic monomer (X) is a compound represented by the following Formula (x-2):

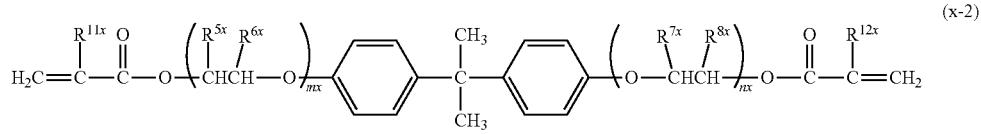

[wherein, in Formula (x-2), each of $R^{5x}$, $R^{6x}$, $R^{7x}$, $R^{8x}$, $R^{11x}$, and $R^{12x}$ independently represents a hydrogen atom or a methyl group; and each of mx and nx independently represents a number from 0 to 4, wherein mx and nx satisfy the relationship: $1 \le (mx+nx) \le 4$].

<6> The photocurable composition according to any one of <1> to <5>, wherein at least one (meth)acrylic monomer configuring the (meth)acrylic monomer (D) is a compound represented by the following Formula (d-1):

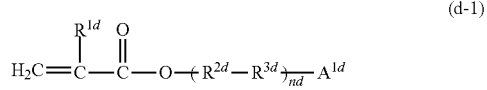

[wherein, in Formula (d-1), $R^{1d}$ represents a hydrogen atom or a methyl group; each $R^{2d}$ independently represents a single bond, or a linear or branched alkylene group having from 1 to 5 carbon atoms; each $R^{3d}$ independently represents a single bond, an ether bond (—O—), an ester bond (—O—(C=O)—), or —$C_6H_4$—O—; $A^{1d}$ represents at least one aromatic ring which may have a substituent; and nd represents a number from 1 to 2].

<7> The photocurable composition according to <6>, wherein the at least one (meth)acrylic monomer configuring the (meth)acrylic monomer (D) is a compound represented by the following Formula (d-2):

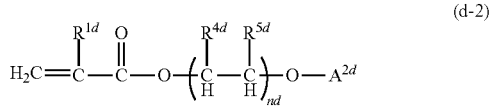

[wherein, in Formula (d-2), each of $R^{1d}$, $R^{4d}$ and $R^{5d}$ independently represents a hydrogen atom or a methyl group; A2d represents at least one aromatic ring which optionally has a substituent; and nd represents a number from 1 to 2].

<8> The photocurable composition according to any one of <1> to <7>, wherein a content of the acrylic monomer (X) is 300 parts by mass or more with respect to 1,000 parts by mass of a total content of the (meth)acrylic monomer component.

<9> The photocurable composition according to any one of <1> to <8>, wherein a content of the acrylic monomer (D) is from 30 parts by mass to 700 parts by mass with respect to 1,000 parts by mass of the total content of the (meth)acrylic monomer component.

<10> The photocurable composition according to any one of <1> to <9>, wherein the photopolymerization initiator is at least one selected from alkylphenone compounds or acylphosphine oxide compounds.

<11> The photocurable composition according to any one of <1> to <10>, wherein a content of the photopolymerization initiator is from 1 part by mass to 50 parts by mass with respect to 1,000 parts by mass of a total content of a (meth)acrylic monomer component.

<12> The photocurable composition according to any one of <1> to <11>, wherein the photocurable composition has a viscosity, as measured using a Type E viscometer at 25° C. and 50 rpm, of from 20 mPa's to 3,000 mPa·s.

<13> The photocurable composition according to any one of <1> to <12>, wherein the photocurable composition is used for production, by stereolithography, of a dental prosthesis, a medical device for intraoral use, or a tooth and jaw model.

<14> The photocurable composition according to any one of <1> to <12>, wherein the photocurable composition is used for production, by stereolithography, of a denture base or a mouthpiece.

<15> The photocurable composition according to any one of <1> to <12>, wherein the photocurable composition is used for production, by stereolithography, of a denture base.

<16> A denture base that is a cured product of the photocurable composition according to <15>.

<17> A plate denture including the denture base according to <16> and an artificial tooth fixed to the denture base.

Advantageous Effects of Invention

One embodiment of the invention provides a photocurable composition which is used in stereolithography, and which has an excellent flexural strength and flexural modulus as well as an excellent fracture toughness after being subjected to photocuring.

Further, one embodiment of the invention provides: a denture base which is a cured product of the above described photocurable composition and which has an excellent flexural strength and flexural modulus as well as an excellent fracture toughness; and a plate denture including the denture base.

DESCRIPTION OF EMBODIMENTS

In the present specification, any numerical range indicated using an expression "from * to" represents a range in which numerical values described before and after the "to" are included in the range as a lower limit value and an upper limit value.

Further, in the present specification, the term "ether bond" refers to a bond in which two hydrocarbon groups are bound via an oxygen atom (a bond represented by —O—), as is commonly defined. Accordingly, "—O—" in an ester bond (—C(=O)—O—) is not included in the definition of the "ether bond".

In the present specification, the term "(meth)acrylic monomer" is a concept which encompasses both an acrylic monomer and a methacrylic monomer.

Further, in the present specification, the term "(meth)acrylate" is a concept which encompasses both acrylate and methacrylate.

Still further, in the present specification, the term "(meth)acryloyloxy group" is a concept which encompasses both acryloyloxy group and methacryloyloxy group.

[Photocurable Composition]

The photocurable composition according to one embodiment of the invention is a photocurable composition for use in stereolithography, wherein the photocurable composition includes:

a (meth)acrylic monomer component including:
  a (meth)acrylic monomer (X) that is at least one selected from di(meth)acrylic monomers containing, within one molecule, two aromatic rings and two (meth)acryloyloxy groups, and that has a weight average molecular weight of from 400 to 580; and
  a (meth)acrylic monomer (D) that is at least one selected from (meth)acrylic monomers containing, within one molecule, at least one aromatic ring and one (meth)acryloyloxy group, and that has a weight average molecular weight of from 140 to 350; and
a photopolymerization initiator.

The photocurable composition according to the present embodiment has an excellent flexural strength and flexural modulus as well as an excellent fracture toughness after being subjected to photocuring, due to containing a combination of the above described acrylic monomer (X) and the above described (meth)acrylic monomer (D).

Accordingly, a stereolithographed product, preferably, a dental prosthesis or the like (namely, a dental prosthesis, a medical device for intraoral use, or a tooth and jaw model; the same shall apply hereinafter; a denture base, in particular) which is produced by stereolithography, using the photocurable composition according to the present embodiment, also has an excellent flexural strength and flexural modulus as well as an excellent fracture toughness.

Further, the photocurable composition according to the present embodiment has a viscosity suitable for the production by stereolithography of a dental prosthesis or the like (an example of a preferred embodiment of the stereolithographed product; the same shall apply hereinafter).

In the present specification, the "(meth)acrylic monomer component" refers to entire (meth)acrylic monomers included in the photocurable composition.

The "(meth)acrylic monomer component" includes at least the (meth)acrylic monomer (X) and the (meth)acrylic monomer (D).

The "(meth)acrylic monomer component" may include a (meth)acrylic monomer other than the (meth)acrylic monomer (X) or the (meth)acrylic monomer (D).

In the photocurable composition according to the present embodiment, the incorporation of the (meth)acrylic monomer (X) allows for improving the flexural strength and flexural modulus after photocuring, as compared to the case in which a (meth)acrylic monomer containing, within one molecule, one aromatic ring and one (meth)acryloyloxy group is incorporated into the composition, instead of the (meth)acrylic monomer (X).

In the photocurable composition according to the present embodiment, the incorporation of the (meth)acrylic monomer (X) allows for preventing a phenomenon in which a crystallinity of the monomers is excessively increased, as compared to the case in which a di(meth)acrylic monomer containing, within one molecule, one aromatic ring and two (meth)acryloyloxy groups is incorporated into the composition, instead of the (meth)acrylic monomer (X). As a result, the viscosity of the photocurable composition is reduced.

In the photocurable composition according to the present embodiment, the incorporation of the (meth)acrylic monomer (X) allows for reducing the viscosity of the photocurable composition, as compared to the case in which a (meth)acrylic monomer containing, within one molecule, three or more aromatic rings is used in the composition, instead of the (meth)acrylic monomer (X).

In the photocurable composition according to the present embodiment, the incorporation of the (meth)acrylic monomer (X) allows for improving the fracture toughness after photocuring, as compared to the case in which a (meth)acrylic monomer containing, within one molecule, three or more (meth)acryloyloxy groups is used in the composition, instead of the (meth)acrylic monomer (X).

The value 580, which is the upper limit of the weight average molecular weight of the (meth)acrylic monomer (X), has been set in terms of the flexural strength and the flexural modulus after photocuring.

The value 400, which is the lower limit of the weight average molecular weight of the (meth)acrylic monomer (X), has been set in terms of ease of production of the monomer or ease of availability.

Further, in the photocurable composition according to the present embodiment, the incorporation of the (meth)acrylic monomer (D) allows for improving the fracture toughness after photocuring.

The value 350, which is the upper limit of the weight average molecular weight of the (meth)acrylic monomer (D), has been set in terms of the flexural strength and the flexural modulus after photocuring.

The value 140, which is the lower limit of the weight average molecular weight of the (meth)acrylic monomer (D), has been set in terms of the ease of production of the monomer or the ease of availability.

The photocurable composition according to the present embodiment preferably satisfies the following flexural strength (namely, bending strength) and the following flexural modulus, after being subjected to photocuring, in terms of the practical use of the resulting dental prosthesis or the like (the resulting denture base, in particular).

In other words, the photocurable composition according to the present embodiment preferably satisfies a flexural strength (bending strength), as measured below, of 60 MPa or more, and more preferably, 65 MPa or more. Specifically, the measurement of the flexural strength (bending strength) is carried out as follows. The photocurable composition is formed into a shaped product having a size of 64 mm×10 mm×3.3 mm thickness, and the resulting shaped product is subjected to UV light irradiation at 10 J/cm² to carry out photocuring, thereby obtaining a stereolithographed product (namely, a cured product; the same shall apply hereinafter). The resulting stereolithographed product is stored in a constant temperature water bath controlled at 37±1° C. for 50±2 hours, and the flexural strength (bending strength) of the stereolithographed product after storage is measured in accordance with ISO 20795-1:2008 (or JIS T 6501:2012).

Further, the photocurable composition according to the present embodiment preferably satisfies a flexural modulus, as measured below, of 1,500 MPa or more, and more preferably, 2,000 MPa or more. Specifically, the measurement of the flexural modulus is carried out as follows. The photocurable composition is formed into a shaped product having a size of 64 mm×10 mm×3.3 mm thickness, and the resulting shaped product is subjected to UV light irradiation at 10 J/cm$^2$ to carry out photocuring, thereby obtaining a stereolithographed product. The resulting stereolithographed product is stored in a constant temperature water bath controlled at 37±1° C. for 50±2 hours, and the flexural modulus of the stereolithographed product after storage is measured in accordance with ISO 20795-1:2008 (or JIS T 6501:2012).

In the present specification, the term "fracture toughness" refers to a total fracture work (an example of unit: J/cm$^2$) obtained by carrying out a fracture toughness test by a flexural test.

The photocurable composition according to the present embodiment preferably satisfies a total fracture work (J/m$^2$), as measured below, of 65 J/m$^2$ or more, and more preferably 70 J/m$^2$ or more, and still more preferably 75 J/m$^2$ or more. Specifically, the measurement of the total fracture work (J/m$^2$) is carried out as follows. The photocurable composition is formed into a shaped product having a size of 39 mm×8 mm×4 mm thickness, and the resulting shaped product is subjected to UV light irradiation at 10 J/cm$^2$ to carry out photocuring, thereby obtaining a stereolithographed product. The resulting stereolithographed product is subjected to Notch processing, and then stored in a constant temperature water bath controlled at 37±1° C. for 7 days±2 hours, and the total fracture work (J/m$^2$) of the stereolithographed product after storage is measured by carrying out a fracture toughness test by a flexural test, at a push-in speed of 1.0±0.2 mm/min, in accordance with ISO 20795-1:2008.

The photocurable composition according to the present embodiment is used for the production, by stereolithography, of a dental prosthesis or the like (namely, a dental prosthesis, a medical device for intraoral use, or a tooth and jaw model).

In the present embodiment, the dental prosthesis may be, for example, a denture base, a denture, an inlay, a crown, a bridge, a temporary crown, or a temporary bridge. Among these, a denture base is preferred.

Further, in the present embodiment, the medical device for intraoral use may be, for example, an orthodontic appliance (such as a mouthpiece, or an orthodontic appliance), a bite splint, a tray for obtaining an impression, or a guide for use in surgery. Among these, an orthodontic appliance is preferred, and a mouthpiece is more preferred.

The dental prosthesis or the like (namely, a dental prosthesis, a medical device for intraoral use, or a tooth and jaw model) is preferably a dental prosthesis or an orthodontic appliance, more preferably a denture base or a mouthpiece, and particularly preferably a denture base.

In the present embodiment, the term "stereolithography" refers to one of the three-dimensional shaping methods utilizing a 3D printer.

Examples of stereolithography methods include an SLA (Stereo Lithography Apparatus) method, a DLP (Digital Light Processing) method, and an ink-jet method.

The photocurable composition according to the present embodiment is particularly suitable for carrying out stereolithography employing an SLA method or a DLP method.

Examples of the SLA method include a method in which a spot-like UV laser beam is irradiated to a photocurable composition to obtain a three-dimensional shaped product.

In a case in which a dental prosthesis or the like is produced by the SLA method, the production thereof may be carried out, for example, as follows. Specifically, the photocurable composition according to the present embodiment is pooled in a container, and a spot-like UV laser beam is selectively irradiated to a liquid surface of the photocurable composition so as to obtain a desired pattern. In this manner, the photocurable composition is cured to form a cured layer having a desired thickness on a shaping table. Subsequently, the shaping table is lowered, and the photocurable composition in a liquid state is supplied over the cured layer, in an amount sufficient for forming one layer, followed by curing the photocurable composition in the same manner as described above. This operation is repeated so as to obtain cured layers disposed one on another in layers. In this manner, a dental prosthesis or the like can be produced.

Examples of the DLP method include a method in which planar light is irradiated to a photocurable composition to obtain a three-dimensional shaped product.

As to the method of obtaining a three-dimensional shaped product by the DLP method, for example, the description in JP-B No. 5111880 and JP-B No. 5235056 can be referred to, as appropriate.

In a case in which a dental prosthesis or the like is produced by the DLP method, the production thereof may be carried out, for example, as follows. Specifically, a lamp which emits light other than a laser beam, such as a high pressure mercury lamp, an ultra-high pressure mercury lamp, or a low pressure mercury lamp, or alternatively, an LED is used as a light source. A planar drawing mask in which a plurality of digital micro mirror shutters are arranged in a plane, is disposed between the light source and the surface of the photocurable composition to be shaped. Then light is irradiated to the surface of the photocurable composition to be shaped through the planar drawing mask, to form a cured layer having a predetermined pattern shape. This operation is repeated so that cured layers are formed and layered one on another, sequentially. In this manner, a dental prosthesis or the like can be produced.

Examples of the ink-jet method include a method in which droplets of a photocurable composition are continuously discharged onto a substrate through an ink-jet nozzle, and then light is irradiated to the droplets adhered to the substrate, to obtain a three-dimensional shaped product.

In a case in which a dental prosthesis or the like is produced by an ink-jet method, the production thereof may be carried out, for example, as follows. Specifically, while scanning a plane with a head including an ink-jet nozzle and a light source, the photocurable composition is discharged onto a substrate through the ink-jet nozzle. At the same time, light is irradiated to the discharged photocurable composition to form a cured layer. This operation is repeated so that cured layers are formed and layered one on another, sequentially. In this manner, a dental prosthesis or the like can be produced.

The photocurable composition according to the present embodiment preferably has a viscosity at 25° C. and 50 rpm, as measured using a Type E viscometer, of from 20 m·Pas to 3,000 mPa's, in terms of suitability for the production, by stereolithography, of a dental prosthesis or the like. The lower limit of the viscosity is more preferably 50 m·Pas. The upper limit of the viscosity is more preferably 2,000 m·Pas, still more preferably 1,500 mPa·s, and particularly preferably 1,200 mPa·s.

The viscosity at 25° C. and 50 rpm of the photocurable composition according to the present embodiment may be adjusted depending on the method of the stereolithography to be used.

In a case in which a dental prosthesis or the like is produced by the SLA method, for example, the viscosity of the photocurable composition is preferably from 50 m·Pas to 3,000 mPa's, more preferably from 50 mPa's to 2,000 m·Pas, still more preferably from 50 m·Pas to 1,500 m·Pas, and particularly preferably from 50 mPa's to 1,200 mPa·s.

In a case in which a dental prosthesis or the like is produced by the DLP method, for example, the viscosity of the photocurable composition is preferably from 50 m·Pas to 500 m·Pas, and more preferably from 50 m·Pas to 250 mPa·s.

In a case in which a dental prosthesis or the like is produced by the ink-jet method, for example, the viscosity of the photocurable composition is preferably from 20 mPa's to 500 m·Pas, and more preferably from 20 mPa's to 100 mPa·s.

Components of the photocurable composition according to the present embodiment will now be described.

< (Meth)acrylic Monomer (X)>

The (meth)acrylic monomer component included in the photocurable composition according to the present embodiment includes the (meth)acrylic monomer (X).

The (meth)acrylic monomer (X) is at least one selected from di(meth)acrylic monomers containing, within one molecule, two aromatic rings and two (meth)acryloyloxy groups, and has a weight average molecular weight of from 400 to 580.

In the photocurable composition according to the present embodiment, the (meth)acrylic monomer (X) mainly contributes to an improvement in the flexural strength and the flexural modulus after photocuring.

The above described (meth)acrylic monomer (X) may consist of one type of di(meth)acrylic monomer containing, within one molecule, two aromatic rings and two (meth)acryloyloxy groups, or may be a mixture composed of two or more types of the di(meth)acrylic monomers.

It is preferable that at least one di(meth)acrylic monomer configuring the (meth)acrylic monomer (X) contains an ether bond within one molecule, in terms of further improving the fracture toughness after photocuring.

Specifically, when the at least one di(meth)acrylic monomer configuring the (meth)acrylic monomer (X) contains an ether bond within one molecule, the degree of freedom of molecular motion is increased to impart flexibility to the cured product after photocuring, thereby improving its toughness. As a result, the fracture toughness of the above described cured product (namely, the fracture toughness of the photocurable composition after photocuring) is improved.

It is more preferable that the at least one di(meth)acrylic monomer configuring the (meth)acrylic monomer (X) contains from one to four ether bonds within one molecule.

When the number of ether bonds within one molecule, in the at least one di(meth)acrylic monomer configuring the (meth)acrylic monomer (X), is four or less, the flexural strength and the flexural modulus after photocuring are further improved.

The number of ether bonds within one molecule is still more preferably from two to four, and particularly preferably from two to three, in terms of further improving the flexural strength and the flexural modulus after photocuring.

It is still more preferable that the at least one di(meth)acrylic monomer configuring the (meth)acrylic monomer (X) is a compound represented by the following Formula (x-1), in terms of reducing the viscosity of the photocurable composition, and further improving the fracture toughness, the flexural strength, and the flexural modulus, after photocuring.

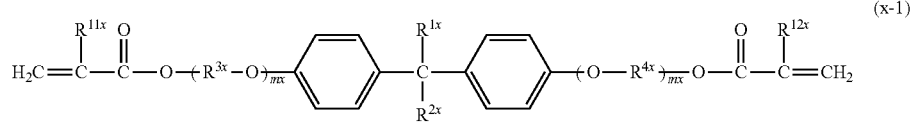

(x-1)

In Formula (x-1), each of $R^{1x}$, $R^{2x}$, $R^{11x}$, and $R^{12x}$ independently represents a hydrogen atom or a methyl group; each of $R^{3x}$ and $R^{4x}$ independently represents a linear or branched alkylene group having from 2 to 4 carbon atoms; and each of mx and nx independently represents a number from 0 to 4, with the proviso that mx and nx satisfy the relationship: $1 \leq (mx+nx) \leq 4$.

In a case in which a plurality of $R^{3x}$s are present in the compound represented by Formula (x-1), the plurality of $R^{3x}$s may be the same as or different from each other. The same applies for $R^{4x}$.

In the Formula (x-1), each of $R^{1x}$ and $R^{2x}$ is preferably a methyl group.

Further, it is preferable that each of $R^{3x}$ and $R^{4x}$ independently represents an ethylene group, a trimethylene group, a tetramethylene group, a 1-methylethylene group, a 1-ethylethylene group or a 2-methyltrimethylene group, and more preferably, an ethylene group or a 1-methylethylene group.

In addition, it is preferable that both of $R^{3x}$ and $R^{4x}$ are ethylene groups, trimethylene groups, tetramethylene groups, 1-methylethylene groups, or 2-methyltrimethylene groups, and more preferably both are ethylene groups or 1-methylethylene groups.

Although the sum of mx+nx is from 1 to 4, it is particularly preferable that the sum of mx+nx is from 2 to 3, in terms of further improving the flexural strength and the flexural modulus after photocuring.

It is still more preferable that the at least one di(meth)acrylic monomer configuring the (meth)acrylic monomer (X) is a compound represented by the following Formula (x-2), in terms of reducing the viscosity of the photocurable composition, and further improving the fracture toughness, the flexural strength, and the flexural modulus, after photocuring.

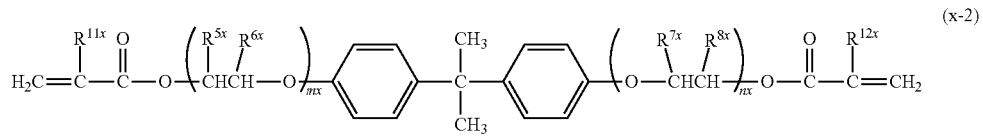

(x-2)

In Formula (x-2), each of $R^{5x}$, $R^{6x}$, $R^{7x}$, $R^{8x}$, $R^{11x}$, and $R^{12x}$ independently represents a hydrogen atom or a methyl group; and each of mx and nx independently represents a number from 0 to 4, with the proviso that mx and nx satisfy the relationship: $1 \le (mx+nx) \le 4$.

In a case in which a plurality of $R^{5x}$s are present in the compound represented by Formula (x-2), the plurality of $R^{5x}$s may be the same as or different from each other. The same applies for each of $R^{6x}$, $R^{7x}$, and $R^{8x}$ In Formula (x-2), it is preferable that one of $R^{5x}$ or $R^{6x}$ is a methyl group, and the other is a hydrogen atom. At the same time, it is preferable that one of $R^{7x}$ or $R^{8x}$ is a methyl group and the other is a hydrogen atom.

In Formula (x-2), it is particularly preferable that $R^{5x}$ and $R^{8x}$ are both methyl groups, and $R^{6x}$ and $R^{7x}$ are both hydrogen atoms.

Although the sum of mx+nx is from 1 to 4, it is particularly preferable that the sum of mx+nx is from 2 to 3, in terms of further improving the flexural strength and the flexural modulus after photocuring.

Specific examples of the (meth)acrylic monomer (X) include ethoxylated bisphenol A di(meth)acrylate (EO=2 mol, 2.2 mol, 2.6 mol, 3 mol, or 4 mol), propoxylated bisphenol A di(meth)acrylate (PO=2 mol, 3 mol, or 4 mol), and ethoxylated bisphenol F di(meth)acrylate (EO=2 mol, 2.2 mol, 2.3 mol, 2.6 mol, 3 mol, or 4 mol).

In the photocurable composition according to the present embodiment, the content of the (meth)acrylic monomer (X) is preferably 100 parts by mass or more, more preferably 300 parts by mass or more, still more preferably 400 parts by mass or more, still more preferably 500 parts by mass or more, and still more preferably 550 parts by mass or more, with respect to 1,000 parts by mass of the total content of the (meth)acrylic monomer component, in terms of reducing the viscosity of the composition, as well as improving the flexural strength and the flexural modulus after photocuring.

The content of the (meth)acrylic monomer (X) is not particularly limited, as long as the content is less than 1,000 parts by mass with respect to 1,000 parts by mass of the total content of the (meth)acrylic monomer component. However, in terms of the fracture toughness after photocuring, the content of the (meth)acrylic monomer (X) is preferably 950 parts by mass or less, more preferably 900 parts by mass or less, and still more preferably 800 parts by mass or less.

< (Meth)acrylic Monomer (D)>

The (meth)acrylic monomer component included in the photocurable composition according to the present embodiment includes the (meth)acrylic monomer (D).

The (meth)acrylic monomer (D) is at least one selected from (meth)acrylic monomers containing, within one molecule, at least one aromatic ring and one (meth)acryloyloxy group, and has a weight average molecular weight of from 140 to 350. The number of aromatic rings contained in one molecule of the (meth)acrylic monomer (D) is not particularly limited, as long as one or more aromatic rings are contained. However, it is preferable that the (meth)acrylic monomer (D) contains from one to three aromatic rings, and more preferably, one or two aromatic rings within one molecule. In a case in which a plurality of aromatic rings are contained within one molecule, the types of the aromatic rings may be the same as or different from each other.

When the (meth)acrylic monomer component contains the (meth)acrylic monomer (D), the fracture toughness after photocuring is markedly improved.

The (meth)acrylic monomer (D) may consist of one type of (meth)acrylic monomer containing, within one molecule, at least one aromatic ring and one (meth)acryloyloxy group, or may be a mixture composed of two or more types of the (meth)acrylic monomers containing, within one molecule, at least one aromatic ring and one (meth)acryloyloxy group.

In the (meth)acrylic monomer (D), the aromatic ring may contain a substituent such as an alkyl group, an aryl group, an alkylaryl group, an aryloxy group, or the like. Further, the (meth)acrylic monomer (D) preferably contains one or two ether bonds or ester bonds (excluding those contained in the acryloyloxy group).

Examples of the (meth)acrylic monomer (D) include phenyl (meth)acrylate, benzyl (meth)acrylate, phenoxyethylene glycol (meth)acrylate, phenoxydiethylene glycol (meth)acrylate, 3-phenoxybenzyl (meth)acrylate, neopentyl glycol (meth)acrylic acid benzoic acid ester, 2-(o-phenylphenoxy)ethyl (meth)acrylate, 2-(1-naphthoxy)ethyl (meth)acrylate, p-cumylphenoxypolyethylene glycol (meth)acrylate, and nonylphenol EO-modified (meth)acrylate (EO=1 mol).

It is preferable that at least one (meth)acrylic monomer configuring the (meth)acrylic monomer (D) is a compound represented by the following Formula (d-1), in terms of further improving the fracture toughness after photocuring.

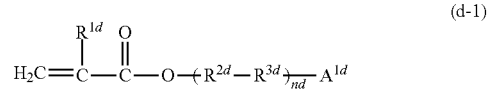

(d-1)

In Formula (d-1), Rid represents a hydrogen atom or a methyl group; each $R^{2d}$ independently represents a single bond, or a linear or branched alkylene group having from 1 to 5 carbon atoms; each $R^{3d}$ independently represents a single bond, an ether bond (namely, —O—), an ester bond (namely, —O—(C=O)—), or —$C_6H_4$—O—; $A^{1d}$ represents an aromatic ring which optionally has a substituent; and nd represents a number from 1 to 2. Examples of the substituent for the aromatic ring represented by $A^{1d}$ include alkyl groups (such as methyl group, ethyl group, propyl group, and butyl group), aryl groups, alkylaryl groups, and aryloxy groups.

Examples of the aromatic ring which optionally has a substituent and which is represented by $A^{1d}$ and include phenyl group, phenyl ether group, biphenyl group, terpenyl group, benzhydryl group, diphenylamino group, benzophenone group, naphthyl group, anthracenyl group or phenanthrenyl group, tolyl group, xylyl group, mesityl group, cumyl group, styryl group, and nonylphenyl group.

The aromatic ring represented by $A^{1d}$ is preferably a phenyl group, a phenyl ether group, a biphenyl group, a naphthyl group, a cumyl group, or a nonylphenyl group.

In addition, it is preferable that the compound represented by Formula (d-1) contains one or two ether bonds or ester bonds (excluding those contained in the acryloyloxy group).

Examples of the linear or branched alkylene group having from 1 to 5 carbon atoms, which is represented by $R^{2d}$, include methylene group, ethylene group, n-propylene group, isopropylene group, n-butylene group, isobutylene group, sec-butylene group, tert-butylene group, n-pentylene group, isopentylene group, neopentylene group, sec-pentylene group, tert-pentylene group and 3-pentylene group. Among these, $R^{2d}$ is preferably a single bond, a methylene group or an ethylene group.

Each $R^{3d}$ is preferably an ether bond or an ester bond.

It is more preferable that the at least one (meth)acrylic monomer configuring the (meth)acrylic monomer (D) is a compound represented by the following Formula (d-2), in terms of further improving the fracture toughness after photocuring.

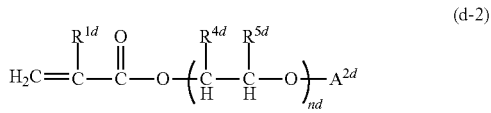

(d-2)

In Formula (d-2), each of Rid, $R^{4d}$ and $R^{5d}$ independently represents a hydrogen atom or a methyl group; A2d represents an aromatic ring which optionally has a substituent; and nd represents a number from 1 to 2.

The scope of the aromatic ring which optionally has a substituent and which is represented by $A^{2d}$, and a preferred scope thereof, are the same as those defined for A1d.

In a case in which a plurality of $R^{4d}$s are present in Formula (d-2), the plurality of $R^{4d}$s may the same as or different from each other. The same applies for $R^{5d}$.

Although the weight average molecular weight of the (meth)acrylic monomer (D) is from 140 to 350, it is preferable that the (meth)acrylic monomer (D) has a weight average molecular weight of from 160 to 300 or less, and more preferably from 160 to 270.

Specific examples of the (meth)acrylic monomer (D) include ethoxylated o-phenylphenol (meth)acrylate, ethoxylated o-phenylphenol EO-modified (meth)acrylate, ethoxylated p-cumylphenol (meth)acrylate, ethoxylated p-nonylphenol (meth)acrylate, ethoxylated p-methylphenol (meth)acrylate, neopentyl glycol-acrylic acid-benzoic acid ester, benzyl (meth)acrylate, m-phenoxybenzyl (meth)acrylate, and 2-(1-naphthoxy)ethyl (meth)acrylate. The term "EO-modified" as used herein means that the compound has a structure of an ethylene oxide unit (namely, —$CH_2$—$CH_2$—O—).

In the photocurable composition according to the present embodiment, the content of the (meth)acrylic monomer (D), with respect to 1,000 parts by mass of the total content of the (meth)acrylic monomer component, is preferably from 10 parts by mass to 800 parts by mass, more preferably from 30 parts by mass to 700 parts by mass, and still more preferably from 100 parts by mass to 600 parts by mass, yet still more preferably from 150 parts by mass to 550 parts by mass, and particularly preferably from 200 parts by mass to 500 parts by mass, in terms of improving the flexural strength, flexural modulus and fracture toughness after photocuring.

Particularly, in a case in which a coloring material is added to the photocurable composition according to the present embodiment, the content of the (meth)acrylic monomer (D) is preferably from 100 to 300 parts by mass with respect to 1,000 parts by mass of the total content of the (meth)acrylic monomer component. In a case in which a coloring material is not added to the photocurable composition according to the present embodiment, the content of the (meth)acrylic monomer (D) is preferably from 400 to 600 parts by mass with respect to 1,000 parts by mass of the total content of the (meth)acrylic monomer component.

Further, the total content of the (meth)acrylic monomer (X) and the (meth)acrylic monomer (D) in the (meth)acrylic monomer component is preferably 50% by mass or more, more preferably 70% by mass or more, still more preferably from 80% by mass or more, and yet still more preferably 90% by mass or more, with respect to the total amount of the (meth)acrylic monomer component. Further, the total content of the (meth)acrylic monomer (X) and the (meth)acrylic monomer (D) may be 100% by mass, with respect to the total amount of the (meth)acrylic monomer component.

The (meth)acrylic monomer component included in the photocurable composition according to the present embodiment may include at least one other (meth)acrylic monomer, other than the (meth)acrylic monomer (X) and the (meth) acrylic monomer (D) described above, to the extent that the effects of the invention are obtained.

<Photopolymerization Initiator>

The photocurable composition according to the present embodiment includes a photopolymerization initiator.

The photopolymerization initiator is not particularly limited, as long as the photopolymerization initiator is capable of generating radicals when irradiated with light. However, the photopolymerization initiator is preferably one which generates radicals when irradiated with light having a wavelength used in the stereolithography.

In general, the wavelength of the light used in the stereolithography may be, for example, from 365 nm to 500 nm. However, the wavelength is preferably from 365 nm to 430 nm, and more preferably from 365 nm to 420 nm, in terms of practical use.

Examples of the photopolymerization initiator which generates radicals when irradiated with light having the wavelength used in the stereolithography include: alkylphenone compounds, acylphosphine oxide compounds, titanocene compounds, oxime ester compounds, benzoin compounds, acetophenone compounds, benzophenone compounds, thioxanthone compounds, a-acyloxime ester compounds, phenylglyoxylate compounds, benzyl compounds, azo compounds, diphenyl sulfide compounds, organic pigment compounds, iron-phthalocyanine compounds, benzoin ether compounds, and anthraquinone compounds.

Among these, an alkylphenone compound and an acylphosphine oxide compound are preferred, in terms of reactivity and the like.

Examples of the alkylphenone compound include 1-hydroxy-cyclohexyl-phenyl-ketone (IRGACURE 184; manufactured by BASF Japan Ltd.).

Examples of the acylphosphine oxide compound include bis(2,4,6-trimethylbenzoyl)-phenylphosphine oxide (IRGACURE 819; manufactured by BASF Japan Ltd.), and 2,4,6-trimethylbenzoyl-diphenyl-phosphine oxide (IRGACURE TPO; manufactured by BASF Japan Ltd.).

The photocurable composition according to the present embodiment may include only one type of the photopolymerization initiator, or two or more types of the photopolymerization initiators.

The content of the photopolymerization initiator (the total content, in a case in which two or more types thereof are included) in the photocurable composition according to the present embodiment is preferably from 1 part by mass to 50 parts by mass, more preferably from 2 parts by mass to 30 parts by mass, still more preferably from 3 parts by mass to 25 parts by mass, and particularly preferably from 5 parts by mass to 25 parts by mass, with respect to 1,000 parts by mass of the total content of the (meth)acrylic monomer component.

<Other Components>

The photocurable composition according to the present embodiment may include at least one other component other than the (meth)acrylic monomer component and the photopolymerization initiator, if necessary.

Note, however, that the total content of the (meth)acrylic monomer component and the photopolymerization initiator is preferably from 60% by mass or more, more preferably from 80% by mass or more, and still more preferably from 90% by mass or more, with respect to the total amount of the photocurable composition.

Examples of the other components include coloring materials.

For example, in a case in which the photocurable composition according to the present embodiment is used for the production of a denture base, the photocurable composition may be colored to a color close to the color of gingival by incorporating a coloring material, in terms of esthetics.

The coloring material is not particularly limited, and examples thereof include pigments, dyes, and colorants. More specific examples of the coloring material include synthetic tar dyes, aluminum lakes of synthetic tar dyes, inorganic pigments, and natural pigments.

Further, examples of the other components also include other curable resins other than the above described (meth) acrylic monomer component (such as other curable monomers other than the above described (meth)acrylic monomer component).

In addition, examples of the other components also include thermal polymerization initiators.

In a case in which the photocurable composition according to the present embodiment includes a thermal polymerization initiator, it is possible to carry out both the photocuring and heat curing in combination. Examples of the thermal polymerization initiator include thermal radical generators and amine compounds.

Still further, examples of the other components include: coupling agents such as silane coupling agents (for example, 3-acryloxypropyltrimethoxysilane); and additives such as rubber agents, ion-trapping agents, ion exchangers, leveling agents, plasticizers, and antifoaming agents.

The method of preparing the photocurable composition according to the present embodiment is not particularly limited. Examples thereof include a method in which the acrylic monomer (X), the (meth)acrylic monomer (D), and the photopolymerization initiator (and other component(s), if necessary) are mixed.

The means for mixing the respective components is not particularly limited. Examples thereof include: dissolution by ultrasonic wave; and mixing utilizing a twin arm mixer, a roll kneader, a twin-screw extruder, a ball mill kneader, or a planetary mixer.

The photocurable composition according to the present embodiment may be prepared by mixing the respective components, then filtering the mixture to remove impurities, and further subjecting the resultant to a vacuum deaeration treatment.

[Photocured Product]

The method of carrying out photocuring using the photocurable composition according to the present embodiment is not particularly limited, and any of known methods and apparatuses can be used. For example, the photocuring may be carried out by a method in which a step of forming a thin film composed of the photocurable composition according to the present embodiment, and a step of obtaining a cured layer by irradiating light to the resulting thin film, are repeated a plurality of times, to dispose a plurality of cured layers one on another in layers, thereby obtaining a photocured product having a desired shape. The thus obtained photocured product may be used as it is, or may be used after being subjected to post-curing by further light irradiation, heating or the like to improve its mechanical properties, morphological stability, and the like.

A glass transition temperature (namely, Tg) after photocuring of the photocurable composition according to the present embodiment is not particularly limited. However, the glass transition temperature (Tg) after photocuring is preferably 70° C. or higher, and more preferably 80° C. or higher, in terms of the flexural strength and the flexural modulus.

At the same time, the glass transition temperature (Tg) after photocuring is preferably 140° C. or lower, in terms of the fracture toughness.

[Denture Base and Plate Denture]

The dental prosthesis or the like which is a cured product (namely, a stereolithographed product) of the photocurable composition according to the present embodiment is particularly preferably a denture base. The denture base which is a cured product of the photocurable composition according to the present embodiment has an excellent flexural strength, flexural modulus and fracture toughness.

The denture base according to the present embodiment may be a denture base for use in a complete denture or a full denture, or alternatively, a denture base for use in a partial denture.

Further, the denture base according to the present embodiment may be a denture base for an upper jaw denture (hereinafter, also referred to as "upper jaw denture base"), or a denture base for a lower jaw denture (hereinafter, also referred to as "lower jaw denture base"), or alternatively, a set of an upper jaw denture base and a lower jaw denture base.

In addition, the denture base according to the present embodiment may be a denture base in which only a portion thereof is made of the photocurable composition according to the present embodiment, or a denture base entirely made of the photocurable composition according to the present embodiment.

Examples of the denture base in which only a portion thereof is made of the photocurable composition according to the present embodiment include: a denture base (a so-called metal base) which includes a metal portion and a resin portion, and in which at least one portion of the resin portion is made of the photocurable composition according to the present embodiment; and a denture base (a so-called resin base) which consists of a resin portion, and in which only a portion of the resin portion is made of the photocurable composition according to the present embodiment.

Examples of the denture base entirely made of the photocurable composition according to the present embodiment include a denture base consisting of a resin portion (a so-called resin base).

A plate denture according to the present embodiment includes the above described denture base according to the present embodiment and an artificial tooth fixed to the denture base.

Thus, the denture base included in the plate denture according to the present embodiment has an excellent flexural strength, flexural modulus and fracture toughness.

The plate denture according to the present embodiment may be a partial denture or a complete denture. In other words, the number of the artificial teeth to be included in the plate denture according to the present embodiment is not particularly limited, as long as the plate denture includes at least one artificial tooth.

Further, the plate denture according to the present embodiment may be an upper jaw denture, or a lower jaw denture, or alternatively, a set of an upper jaw denture and a lower jaw denture.

Examples of materials for the artificial tooth include an acrylic resin.

Further, the artificial tooth may contain a filler and/or the like, in addition to the acrylic resin.

Examples

The present invention will now be described more specifically, with reference to Examples. However, the invention is in no way limited to these Examples.

[Examples 1 to 18 and Comparative Examples 1 to 8]
<Preparation of Photocurable Compositions >

The components shown in the following Tables 1 to 3 were mixed to obtain photocurable compositions of Examples and Comparative Examples.
<Measurements and Evaluations>

The following measurements and evaluations were performed, using each of the resulting photocurable compositions. The results are shown in Tables 1 to 3.
(Viscosity of Photocurable Compositions)

The viscosity of each of the photocurable compositions was measured by a Type E viscometer, under conditions of 25° C. and 50 rpm.
(Flexural Strength and Flexural Modulus of Stereolithographed Products)

Each of the resulting photocurable compositions was shaped into a size of 64 mm×10 mm×3.3 mm thickness using a 3D printer (MASTER PLUS S 2011; manufactured by Carima Co., Ltd.), to obtain a shaped product. The resulting shaped product was irradiated with UV light having a wavelength of 365 nm, at 10 J/cm², to carry out main curing, thereby obtaining a stereolithographed product.

The resulting stereolithographed product (hereinafter, referred to as "test piece") was stored in a constant temperature water bath maintained at 37±1° C. for 50±2 hours.

Then, the test piece was retrieved from the constant temperature water bath, and the flexural strength and the flexural modulus of each of the retrieved test piece were measured in accordance with ISO 20795-1:2008. These measurements were carried out using a tensile tester (manufactured by INTESCO Co., Ltd.) at a tensile speed of 5+1 mm/min.

In a case in which each of the above obtained photocurable compositions is used in the production of a dental prosthesis or the like (a denture base, in particular), the resulting dental prosthesis or the like preferably has a flexural strength as measured above of 60 MPa or more, and more preferably 65 MPa or more.

Further, in this case, the resulting dental prosthesis or the like preferably has a flexural modulus as measured above of 1,500 MPa or more, and more preferably 2,000 MPa or more.
(Total Fracture Work Measured by Fracture Toughness Test by Flexural Test)

Each of the resulting photocurable compositions was shaped into a size of 39 mm×8 mm×4 mm thickness using a 3D printer (MASTER PLUS S 2011; manufactured by Carima Co., Ltd.), to obtain a shaped product. The resulting shaped product was irradiated with UV light having a wavelength of 365 nm, at 10 J/cm², to carry out main curing of the shaped product, thereby obtaining a stereolithographed product.

The resulting stereolithographed product (hereinafter, referred to as "test piece") was subjected to Notch processing, and then stored in a constant temperature water bath controlled at 37±1° C. for 7 days±2 hours in accordance with ISO 20795-1:2008.

Then, the test piece was retrieved from the constant temperature water bath, and the retrieved test piece was subjected to a fracture toughness test by a flexural test in accordance with ISO 20795-1:2008, to measure the total fracture work (J/m²) thereof. The fracture toughness test by a flexural test (namely, the measurement of the total fracture work) was carried out using a tensile tester (manufactured by INTESCO Co., Ltd.) at a push-in speed of 1.0±0.2 mm/min.

In the above described measurement, a higher numerical value of the total fracture work indicates a higher fracture toughness.

In a case in which each of the above obtained photocurable compositions is used in the production of a dental prosthesis or the like (a denture base, in particular), the resulting dental prosthesis or the like preferably has a total fracture work as measured above of 65 J/m² or more, more preferably 70 J/m² or more, and particularly preferably 75 J/m² or more.

TABLE 1

|  |  |  | Mw | Example 1 | Example 2 | Example 3 | Example 4 | Example 5 | Example 6 | Example 7 | Example 8 | Example 9 |
|---|---|---|---|---|---|---|---|---|---|---|---|---|
| Composition | (Meth)acrylic monomer (X) | ABE-300 | 468.6 | 700 |  |  | 700 | 600 |  |  |  |  |
|  |  | A-BPE-4 | 512.6 |  | 800 | 700 |  |  | 600 | 500 |  |  |
|  |  | A-BPE-3 | 510.6 |  |  |  |  |  |  |  | 800 |  |
|  |  | BP-4PA | 568.7 |  |  |  |  |  |  |  |  | 900 |
|  |  | BPF2.3 | 409.7 |  |  |  |  |  |  |  |  |  |
|  |  | BP-2EM | 479.0 |  |  |  |  |  |  |  |  |  |
|  | (Meth)acrylic monomer (D) | BZA | 162.2 | 300 | 200 | 300 |  |  |  |  |  |  |
|  |  | PO-A | 192.2 |  |  |  | 300 |  |  |  |  |  |
|  |  | POB-A | 254.3 |  |  |  |  | 400 |  |  | 200 | 100 |
|  |  | A-LEN-10 | 268.3 |  |  |  |  |  | 400 | 500 |  |  |
|  |  | BZ | 176.2 |  |  |  |  |  |  |  |  |  |
|  |  | PO | 206.2 |  |  |  |  |  |  |  |  |  |

TABLE 1-continued

|  |  | Mw | Example 1 | Example 2 | Example 3 | Example 4 | Example 5 | Example 6 | Example 7 | Example 8 | Example 9 |
|---|---|---|---|---|---|---|---|---|---|---|---|
|  | Photopolymerization initiator | Irg819 |  10 | 10 | 10 | 10 | 10 | 10 | 10 | 10 | 10 |
|  |  | Irg184 |  |  |  |  |  |  |  |  |  |
|  |  | TPO |  |  |  |  |  |  |  |  |  |
| Evaluation | (1) Viscosity (mPa·s) |  | 260 | 320 | 210 | 180 | 180 | 500 | 410 | 1100 | 1120 |
|  | (2) Flexural strength (MPa) |  | 80 | 74 | 67 | 74 | 73 | 79 | 68 | 66 | 66 |
|  | (3) Flexural modulus (MPa) |  | 510 | 2520 | 2405 | 2400 | 2660 | 2560 | 2750 | 2230 | 2150 |
|  | (4) Total fracture work (J/m$^2$) |  | 168 | 181 | 245 | 151 | 206 | 181 | 350 | 178 | 169 |

TABLE 2

|  |  | Mw | Example 10 | Example 11 | Example 12 | Example 13 | Example 14 | Example 15 | Example 16 | Example 17 | Example 18 |
|---|---|---|---|---|---|---|---|---|---|---|---|
| Composition | (Meth)acrylic monomer (X) | ABE-300 | 468.6 |  |  |  |  |  | 500 |  | 350 |  |
|  |  | A-BPE-4 | 512.6 |  |  |  | 700 | 700 |  | 600 |  |  |
|  |  | A-BPE-3 | 510.6 |  |  |  |  |  |  |  |  |  |
|  |  | BP-4PA | 568.7 |  |  |  |  |  |  |  |  |  |
|  |  | BPF2.3 | 409.7 | 700 | 600 |  |  |  |  |  |  |  |
|  |  | BP-2EM | 479.0 |  |  | 500 |  |  |  |  |  | 450 |
|  | (Meth)acrylic monomer (D) | BZA | 162.2 |  |  |  |  |  |  |  |  |  |
|  |  | PO-A | 192.2 |  |  | 500 |  |  |  |  |  |  |
|  |  | POB-A | 254.3 | 300 |  |  |  |  | 400 |  |  | 550 |
|  |  | A-LEN-10 | 268.3 |  | 400 |  |  |  |  | 400 | 650 |  |
|  |  | BZ | 176.2 |  |  |  | 300 |  |  |  |  |  |
|  |  | PO | 206.2 |  |  |  |  | 300 |  |  |  |  |
|  | Photopolymerization initiator | Irg819 |  | 10 | 10 | 10 | 10 | 10 |  |  | 10 | 10 |
|  |  | Irg184 |  |  |  |  |  |  | 10 | 10 |  |  |
|  |  | TPO |  |  |  |  |  |  | 10 | 10 |  |  |
| Evaluation | (1) Viscosity (mPa·s) |  | 320 | 540 | 50 | 230 | 240 | 190 | 510 | 310 | 80 |
|  | (2) Flexural strength (MPa) |  | 72 | 73 | 67 | 75 | 73 | 71 | 77 | 66 | 67 |
|  | (3) Flexural modulus (MPa) |  | 2330 | 2535 | 2245 | 2630 | 2530 | 2580 | 2530 | 2510 | 2305 |
|  | (4) Total fracture work (J/m$^2$) |  | 235 | 228 | 164 | 153 | 155 | 224 | 219 | 509 | 160 |

TABLE 3

|  |  | Mw | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|
| Composition | (Meth)acrylic monomer (X) | ABE-300 | 468.6 | 1000 |  |  |  |  | 700 | 800 |  |
|  |  | A-BPE-4 | 512.6 |  |  |  |  |  |  |  |  |
|  |  | A-BPE-3 | 510.6 |  | 1000 |  |  |  |  |  |  |
|  |  | BP-4PA | 568.7 |  |  |  |  |  |  |  |  |
|  |  | BPF2.3 | 409.7 |  |  | 1000 |  |  |  |  |  |
|  |  | BP-2EM | 479.0 |  |  |  | 1000 |  |  | 700 | 800 |
|  | (Meth)acrylic monomer (D) | BZA | 162.2 |  |  |  |  |  |  |  |  |
|  |  | PO-A | 192.2 |  |  |  |  |  |  |  |  |
|  |  | POB-A | 254.3 |  |  |  |  |  |  |  |  |
|  |  | A-LEN-10 | 268.3 |  |  |  |  |  |  |  |  |
|  |  | BZ | 176.2 |  |  |  |  |  |  |  |  |
|  |  | PO | 206.2 |  |  |  |  |  |  |  |  |
|  | (Meth)acrylic monomer | AIB | 128.2 |  |  |  |  | 300 |  | 300 |  |
|  |  | LA | 240.4 |  |  |  |  | 200 |  |  | 200 |
|  | Photopolymerization initiator | Irg819 |  | 10 | 10 | 10 | 10 | 10 | 10 | 10 | 10 |
|  |  | Irg184 |  |  |  |  |  |  |  |  |  |
|  |  | TPO |  |  |  |  |  |  |  |  |  |
| Evaluation | (1) Viscosity (mPa·s) |  | 1540 | 3240 | 950 | 950 | 190 | 250 | 120 | 160 |

TABLE 3-continued

|  | Mw | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| (2) Flexural strength (MPa) |  | 88 | 80 | 82 | 95 | 65 | 62 | 68 | 63 |
| (3) Flexural modulus (MPa) |  | 2465 | 2400 | 2470 | 2840 | 2105 | 1950 | 2250 | 2180 |
| (4) Total fracture work (J/m²) |  | 45 | 57 | 72 | 28 | 65 | 54 | 52 | 44 |

In Tables 1 to 3, each of the numbers shown in the fields of "Composition of photocurable composition" in the respective Examples and Comparative Examples is indicated in "parts by mass".

The respective structures of the (meth)acrylic monomers (X) listed in Tables 1 to 3 are as shown below.

In Tables 1 to 3, ABE-300, A-BPE-4, and A-BPP-3 are acrylic monomers manufactured by Shin-Nakamura Chemical Co., Ltd.; BP-4PA is an acrylic monomer manufactured by Kyoeisha Chemical Co., Ltd.; BP-2EM is a methacrylic monomer manufactured by Kyoeisha Chemical Co., Ltd.; and BPF 2.3 is an acrylic monomer manufactured by DKS. Co. Ltd.

In Tables 1 to 3, BZA, which is the (meth)acrylic monomer (D), is an acrylic monomer manufactured by Osaka Organic Chemical Industry Ltd.; PO-A, POB-A, and BZ are acrylic monomers manufactured by Kyoeisha Chemical Co., Ltd.; PO is a methacrylic monomer manufactured by Kyoeisha Chemical Co., Ltd.; and A-LEN-10 is an acrylic monomer manufactured by Shin-Nakamura Chemical Co., Ltd.; and the structures thereof are as shown below.

The structure of the above described (meth)acrylic monomers (D) are as shown below.

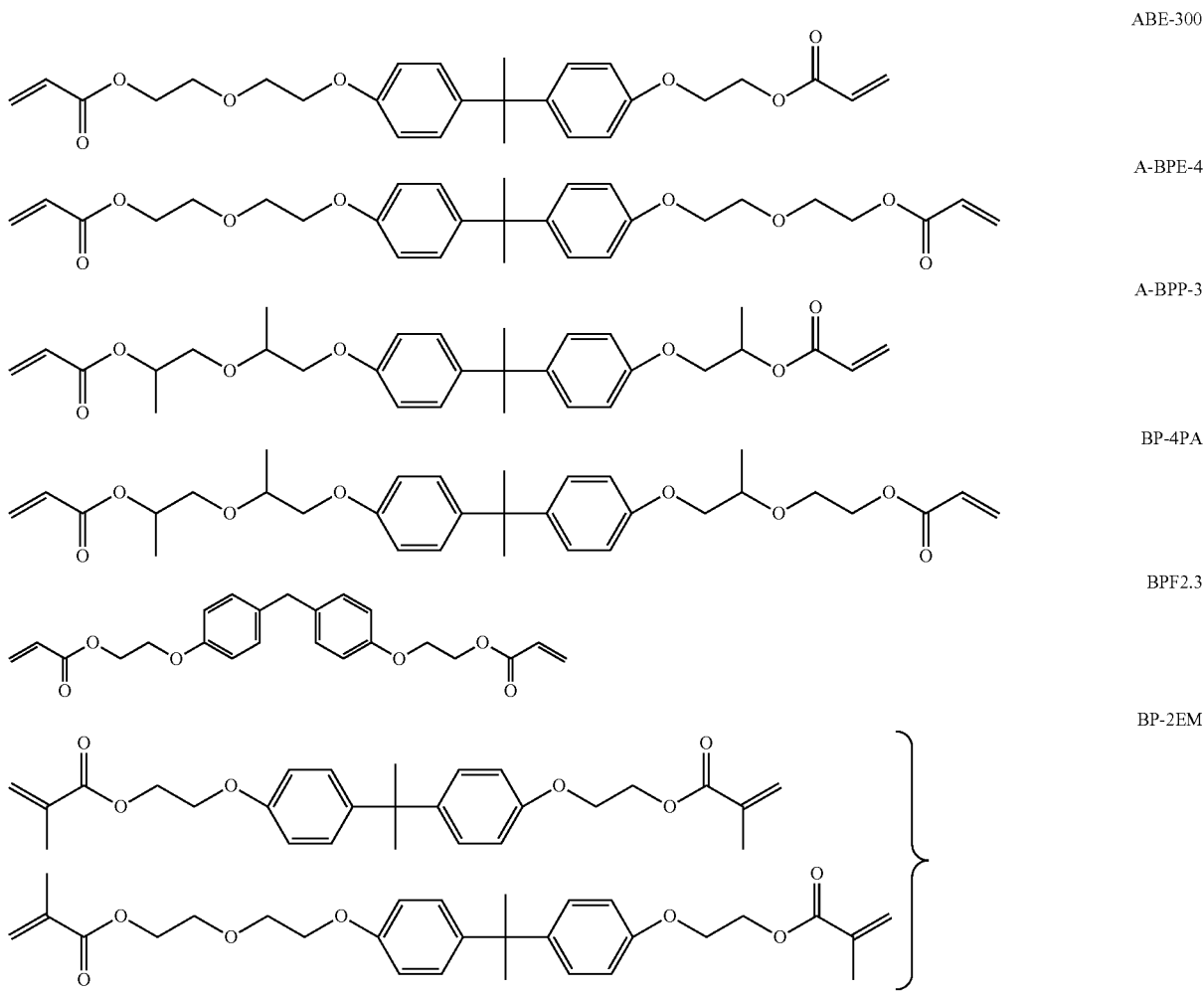

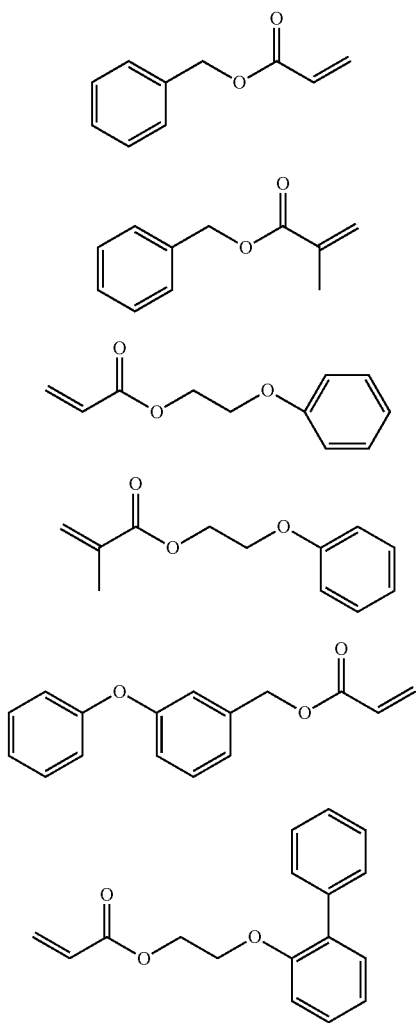

BZA

BZ

PO-A

PO

POB-A

A-LEN-10

AIB and LA, which are (meth)acrylic monomers used in Comparative Example 5 to Comparative Example 8 are acrylic monomers manufactured by Osaka Organic Chemical Industry Ltd.; and the structures thereof are as shown below.

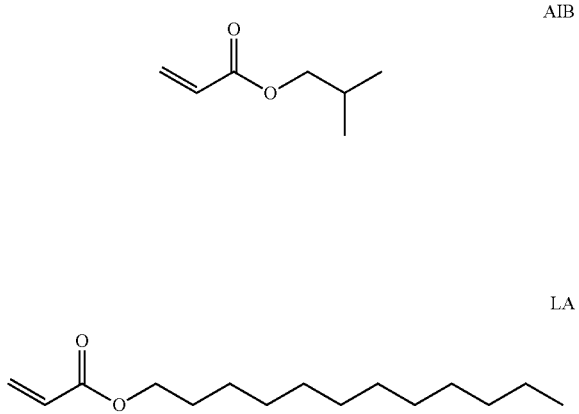

AIB

LA

The respective structures of the photopolymerization initiators listed in Tables 1 to 3 are as shown below.

In Tables 1 to 3, Irg 819 is "IRGACURE 819" (an acylphosphine oxide compound) manufactured by BASF Japan Ltd.; Irg 184 is "IRGACURE 184" (an alkylphenone compound) manufactured by BASF Japan Ltd.; and TPO is "IRGACURE TPO" (an acylphosphine oxide compound) manufactured by BASF Japan Ltd.

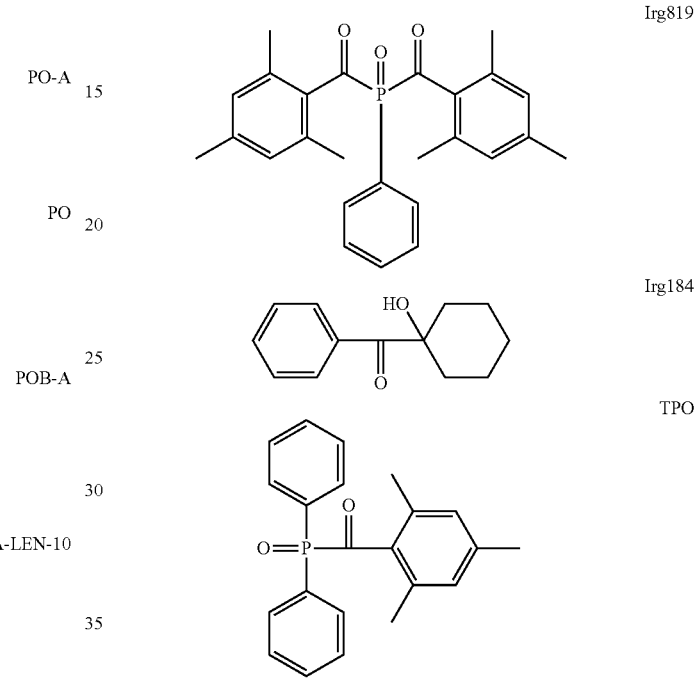

Irg819

Irg184

TPO

As shown in Tables 1 to 3, in Examples 1 to 16, in each of which a photocurable composition including the (meth) acrylic monomer (X) and the (meth)acrylic monomer (D) was used, it was possible to obtain stereolithographed products having an excellent flexural strength (specifically, 65 MPa or more), an excellent flexural modulus (specifically, 2,000 MPa or more), and an excellent fracture toughness (specifically, a total fracture work of 75 $J/m^2$ or more). Further, the photocurable compositions of Examples 1 to 16 had a viscosity suitable for stereolithography.

The above results confirmed that each of the photocurable compositions of Examples 1 to 18 is suitable for the production, by stereolithography, of a dental prosthesis or the like (a denture base, in particular).

In contrast to Examples 1 to 18, in Comparative Examples 1 to 4, in each of which a photocurable composition not including a (meth)acrylic monomer other than the (meth) acrylic monomer (X) was used, the fracture toughness of the resulting stereolithographed products was reduced.

In addition, in Comparative Examples 5 to 8, in each of which a (meth)acrylic monomer other than the (meth)acrylic monomer (D) was used, instead of the (meth)acrylic monomer (D), the fracture toughness of the resulting stereolithographed products was reduced.

The disclosure of Japanese Patent Application No. 2017-066065 is incorporated herein by reference in their entirety.

All publications, patent applications, and technical standards mentioned in the present specification are incorporated herein by reference to the same extent as if such individual publication, patent application, or technical standard was specifically and individually indicated to be incorporated by reference. The foregoing description of the exemplary embodiments of the present invention has been provided for the purposes of illustration and description, and is not intended to be exhaustive or to limit the invention to the precise forms disclosed. It is obvious that many modifications and variations will be apparent to those skilled in the art. The above-described embodiments were chosen and described in order to best explain the principles and practical applications of the invention, and to enable others of ordinary skills in the art to understand the invention in various embodiments with various modifications as are suited to the particular use contemplated. It is intended that the scope of the invention be defined by the following claims and their equivalents.

The invention claimed is:

1. A photocurable composition for use in stereolithography, the photocurable composition comprising:
 a (meth)acrylic monomer (X) that is at least one selected from the group consisting of di(meth)acrylic monomers containing, within one molecule, two aromatic rings and two (meth)acryloyloxy groups, and that has a weight average molecular weight of from 400 to 580;
 a (meth)acrylic monomer (D) that is at least one selected from the group consisting of (meth)acrylic monomers containing, within one molecule, at least one aromatic ring and one (meth)acryloyloxy group, and that has a weight average molecular weight of from 140 to 350; and
 a photopolymerization initiator,
 wherein a total content of the (meth)acrylic monomer (X) and the (meth)acrylic monomer (D) in the (meth) acrylic monomer component is 80% by mass or more, with respect to a total amount of the (meth) acrylic monomer component,
 wherein a content of the (meth)acrylic monomer (D), with respect to 1,000 parts by mass of a total content of (meth)acrylic monomer component, is from 100 parts by mass to 600 parts by mass, and
 wherein the photocurable composition has a viscosity, as measured using a Type E viscometer at 25° C. and 50 rpm, of from 20 m·Pas to 3,000 mPa·s.

2. The photocurable composition according to claim 1, wherein at least one di(meth)acrylic monomer configuring the (meth)acrylic monomer (X) contains an ether bond within one molecule.

3. The photocurable composition according to claim 1, wherein at least one di(meth)acrylic monomer configuring the (meth)acrylic monomer (X) contains from one to four ether bonds within one molecule.

4. The photocurable composition according to claim 1, wherein at least one di(meth)acrylic monomer configuring the (meth)acrylic monomer (X) is a compound represented by the following Formula (x-1):

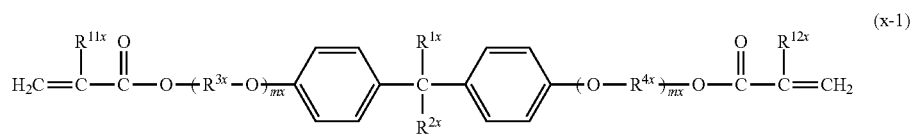

wherein, in Formula (x-1), each of $R^{1x}$, $R^{2x}$, $R^{11x}$, and $R^{12x}$ independently represents a hydrogen atom or a methyl group; each of $R^{3x}$ and $R^{4x}$ independently represents a linear or branched alkylene group having from 2 to 4 carbon atoms; each of mx and nx independently represents a number from 0 to 4; and mx and nx satisfy the relationship: $1 \leq (mx+nx) \leq 4$.

5. The photocurable composition according to claim 1, wherein at least one di(meth)acrylic monomer configuring the (meth)acrylic monomer (X) is a compound represented by the following Formula (x-2):

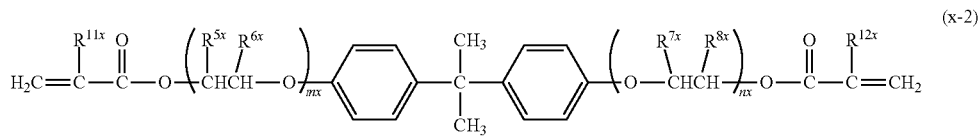

wherein, in Formula (x-2), each of $R^{5x}$, $R^{6x}$, $R^{7x}$, $R^{8x}$, $R^{11x}$, and $R^{12x}$ independently represents a hydrogen atom or a methyl group; each of mx and nx independently represents a number from 0 to 4; and mx and nx satisfy the relationship: $1 \leq (mx+nx) \leq 4$.

6. The photocurable composition according to claim 1, wherein at least one (meth)acrylic monomer configuring the (meth)acrylic monomer (D) is a compound represented by the following Formula (d-1):

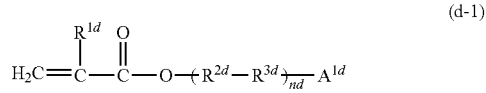

wherein, in Formula (d-1), $R^{1d}$ represents a hydrogen atom or a methyl group; each $R^{2d}$ independently represents a single bond, or a linear or branched alkylene group having from 1 to 5 carbon atoms; each $R^{3d}$ independently represents a single bond, an ether bond (—O—), an ester bond (—O—(C=O)—), or —$C_6H_4$—O—; $A^{1d}$ represents at least one aromatic ring which may have a substituent; and nd represents a number from 1 to 2.

7. The photocurable composition according to claim 1, wherein the at least one (meth)acrylic monomer configuring the (meth)acrylic monomer (D) is a compound represented by the following Formula (d-2):

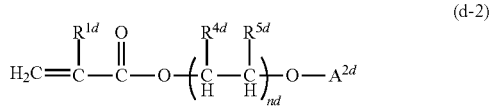

(d-2)

wherein, in Formula (d-2), each of $R^{1d}$, $R^{4d}$ and $R^{5d}$ independently represents a hydrogen atom or a methyl group; $A^{2d}$ represents at least one aromatic ring which may have a substituent;
and nd represents a number from 1 to 2.

8. The photocurable composition according to claim 1, wherein a content of the (meth)acrylic monomer (X) is 300 parts by mass or more with respect to 1,000 parts by mass of a total content of a (meth)acrylic monomer component.

9. The photocurable composition according to claim 1, wherein a content of the (meth)acrylic monomer (D) is from 30 parts by mass to 700 parts by mass with respect to 1,000 parts by mass of a total content of a (meth)acrylic monomer component.

10. The photocurable composition according to claim 1, wherein the photopolymerization initiator is at least one selected from the group consisting of alkylphenone compounds and acylphosphine oxide compounds.

11. The photocurable composition according to claim 1, wherein a content of the photopolymerization initiator is from 1 part by mass to 50 parts by mass with respect to 1,000 parts by mass of a total content of a (meth)acrylic monomer component.

12. The photocurable composition according to claim 1, wherein the photocurable composition is used for production, by stereolithography, of a dental prosthesis, a medical device for intraoral use, or a tooth and jaw model.

13. The photocurable composition according to claim 1, wherein the photocurable composition is used for production, by stereolithography, of a denture base or a mouthpiece.

14. The photocurable composition according to claim 1, wherein the photocurable composition is used for production, by stereolithography, of a denture base.

15. A denture base that is a cured product of the photocurable composition according to claim 14.

16. A plate denture comprising the denture base according to claim 15 and an artificial tooth fixed to the denture base.

* * * * *